United States Patent [19]

Poschel et al.

[11] 4,434,169

[45] Feb. 28, 1984

[54] PHARMACEUTICAL COMPOSITIONS AND METHODS

[75] Inventors: Bruno P. H. Poschel; Donald E. Butler, both of Ann Arbor, Mich.

[73] Assignee: Warner-Lambert Company, Morris Plains, N.J.

[21] Appl. No.: 455,396

[22] Filed: Jan. 3, 1983

[51] Int. Cl.$^3$ ............................................. A61K 31/44
[52] U.S. Cl. .................................................... 424/263
[58] Field of Search ......................................... 424/263

[56] References Cited

U.S. PATENT DOCUMENTS

4,067,983  1/1978  Poschel ............................... 424/263

Primary Examiner—Stanley J. Friedman
Attorney, Agent, or Firm—Ronald A. Daignault

[57] ABSTRACT

Oral pharmaceutical compositions comprising microdoses of 3-phenoxypyridine or pharmaceutically acceptable acid-addition salts thereof and a pharmaceutical carrier. Methods for treating hippocampal dysfunctions by administering microdoses of 3-phenoxypyridine or a pharmaceutically acceptable acid-addition salt thereof.

5 Claims, 14 Drawing Figures

OLD RATS HIPPOCAMPAL SPECTRA

OLD RATS CORTICAL SPECTRA

FIG. 4D

5th DAY DOSE (120 MIN POST)

FIG. 4Z

5th DAY DOSE (120 MIN POST)

FIG. 4C

3RD DAY DOSE (120 MIN POST)

FIG. 4Y

3RD DAY DOSE (120 MIN POST)

FIG. 4B

1ST DAY DOSE (120 MIN POST)

FIG. 4X

1ST DAY DOSE (120 MIN POST)

FIG. 4A

PRETREATMENT

FIG. 4W

PRETREATMENT

PHARMACEUTICAL COMPOSITIONS AND METHODS

SUMMARY AND DETAILED DESCRIPTION

The present invention relates to oral pharmaceutical compositions capable of normalizing hippocampal function and to methods for treating hippocampal dysfunctions.

More particularly, the invention relates to pharmaceutical composition and methods employing microdoses of 3-phenoxyyridine, a known compound which is represented by the formula or a pharmaceutically acceptable acid-addition salt thereof. Some typical examples of pharmaceutically acceptable acid-addition salt forms are the hydrochloride, monosulfate, citraconate, maleate, p-toluene sulfonate, and methane sulfonate salts. The preferred salt being the monosulfate salt.

In addition, the 3-phenoxypyridine and its acid-addition salts can exist in anhydrous forms as well as in solvated, including hydrated, forms. In general, the hydrated forms and the solvated forms with pharmaceutically-acceptable solvents are equivalent to the anhydrous or unsolvated form for the purposes of the invention. A typical hydrate would be the aforementioned hydrochloride in the form of its hydrate.

In addition, 3-phenoxypyridine compounds may exist in more than one crystalline form, such as the monosulfate, mp 114.5°–117° C. and mp 107°–109° C., and all forms are intended to be included within the scope of this invention.

3- Phenoxypyridine and pharmaceutically acceptable salts thereof are known compounds. [Renshaw and Conn, J. Am. Chem. Soc. 59, 197 (1937), Butler et al, J. Med. Chem.; 14, 575 (1971), and Butler et al, J. Med. Chem.; 24, 346 (1981)]. The preferred pharmaceutically acceptable salt is the subject matter of U.S. Pat. No. 4,129,555, issued Dec, 5, 1978, which is incorporated by reference. The use of 3-phenoxypyridine and its pharmaceutically acceptable salts for psychostimulation is reported in U.S. Pat. No. 4,067,983, issued Jan. 10. 1987, which is incorporated by reference.

Based upon a modified learning and memory test procedure which is generally described in "Psychological Reports," 14, 731 (1964) and in "Science," 178 518 (1972) and a test for psychostimulation repored in "Life Sciences," 3 903 (1964), U.S. Pat. No. 4,067,983, was obtained for methods of using 3-phenoxypyridine and pharmaceutically acceptable salts thereof for inducing psychostimulation. The term "inducing psychostimulation," as defined in the patent is intended to mean the following:

a. Causing a calming effect in hyperactive individuals, preferably children.

b. Elevation of mood in subjects suffering from mental depression.

c. Increasing the degree of alertness in subjects exhibiting senility or mental fatique.

In addition, U.S. Pat. No. 4,067,983 teaches how to use 3- phenoxypyridine and its pharmaceutically acceptable salts for inducing psychostimulation.

"The aforementioned compounds and compositions are administered orally, in dosage unit form, with the dose adjusted to the needs and tolerances of the individual patient. The usual mammalian dosege range for a 70 kg subject is from 3.5 to 2,000 mg per day (0.05 mg to 29 mg per kg of weight per day), preferably 25 to 750 mg per day (0.36 mg to 10.7 mg per kg of weight per day), optionally in divided portions.

When the aforementioned compounds and compositions of this invention are administered to normal human subjects to overcome fatigue or boredom, dosages on the lower side of the aforementioned dosage range are preferred (3.5 to 500 mg per day, 0.05 mg to 7 mg per kg per day) while in the treatment of depression dosages on the higher side of the dose range are preferred (1,000 to 2,000 mg per day, 14 mg to 29 mg per kg of weight per day)."

More recently, other scientists have reported an additional study with 3-phenoxypridine (CI-844) in a learning test using a single dose of 30 mg per kg per day (Boff, et al, Abst. 87.7, p 320; Abst; Soc. for Neuroscience, 12th Annual Meeting, 1982).

The common symptoms of patients with normal senility and with senile organic brain syndrom can be grouped as follows:

A. Confusion, disorientation in space and/or time.

B. Forgetfulness, poor memory, memory loss.

C. Poor attention or distractibility.

D. Affective disturbances (agitation, depression, apathy, lethargy).

These groupings are derived from a section in Diagnostic and Statistical Manual of Mental Disorders; R. L. Spitzer 1980, 107–113.

As shown by the above description, "senility is not a monolithic disease, it is a complex of a number of symptoms which may be interrelated." It is considered that a single drug will not cope with the entire range of symptomatology. Thus drugs have to be designed to cope with (1) memory loss, (2) amnesia, (3) disorientation, (4) benign senescent forgethfulness, (5) affective disturbance, as well as (6) the almost totally debilitaing senile dementia of the Alzheimer Type (SDAT). A drug dealing with any of the above would be beneficial in the treatment of senile patients, provided that the patients exhibit the partucular symptom or symptoms the drug ameliorates. In treating patients with multiple symptoms, one would seek a drug having activity against a number of symptoms wherein the profile of activity matches as close as possible the profile of symptoms. In addition, in designing any drug to treat a disease state, one would also try to employ as low a dosage regimen as possible to minimize complications, side effects, or systemic toxicity. This is especially true in the treatment of geriatric patients, since the elderly are generally of fragile health and incapable of withstanding signiicant drug toxicity. In addition, the use of low doses is especially important in long-term types of thereapy such as the treatment of senility. Thus dealing with the treatment of senility in the aged, the use of low dosage regimens is especially desirable.

Since the earlier invention leading to U.S. Pat. No. 4,067,983, 3-phenoxypyridine and its pharmaceutically acceptable salts has yielded certain very unexpected biological activities after evaluation in three different tests: two behavioral models and one electroencephalographic (EEG) test.

It has been found that while 3-phenoxypyridine and its pharmaceutically acceptable salts (studies specifically employed 3-phenoxypyridine monosulfate) at the dose range disclosed in the earlier patent, U.S. Pat. No. 4,067,983, clearly affects certain symptoms associated with senility, 3-phenoxypyridine and its pharmaceutically acceptable salts (studies specifically employed 3-phenoxypyridine monosulfate) at extremely low dosages affects other symptoms associated with senility. Even more surprising, as the dosage in the models is increased from these extremely low dosages, certain of the effects on symptoms associated with senility are diminished. Thus as one moves upward in dosages from extremely low dosages showing a pharmacologic profile for treating symptoms of senility of a certain type, a different pharmacologic profile is obtained for treating symptoms of senility, some symptoms being the same and others different. This activity at extremely low dosages is especially astounding for a very simple organic molecule when contrasted to most other extremely active organic molecules which almost invariably have extremely complex structures.

More specifically, it has been found in animal models that 3-phenoxypyridine and its pharmaceutically acceptable salts diminish certain symptoms associated with senility at a dose range of 0.0002 mg/kg to 0.03 mg/kg of body weight per day, preferably 0.0005 mg/kg to 0.01 mg/kg. The specific symptoms that are ameliorated by the use of 3-phenoxypyridine and its pharmaceutically acceptable salts are loss of memory, diminution of confusion and disorientation. It also should be noted that when moving from the dose range of the U.S. Pat. No. 4,067,983 to the dose range of this invention, one will no longer (1) overcome fatigue or boredom in senility, (2) calm hyperactive individuals, or (3) elevate mood of depressed subjects, while higher dose ranges do not exhibit the reversal of memory loss which is found at the extremely low doses.

When administered in dosage unit form, the usual mammalian (such as rats, cats, dogs, monkeys, etc) dosage range for a 70 kg subject is from 0.014 to 2.1 mg per day (0.0002 mg to 0.03 mg per kg of weight per day), preferably 0.035 to 0.7 mg per day (0.0005 to 0.01 mg per kg of weight per day), optionally in divided portions.

It appears that 3-phenoxypyridine and pharmaceutically-acceptable acid-addition salts thereof ameliorates disturbed hippocampal function when administered at extremely low dosages. Therefore, 3-phenoxypyridine and pharmaceutically-acceptable acid-addition salts thereof would be useful in the treatment of disorders involving hippocampal dysfunction, such as benigh senescent forgetfulness and senile dementia of the Alzheimer type (SDAT), which are characterized by memory loss, disorientation (dislocation as to time and place) and confusion (failure to distinguish between different events, persons, ideas, times, etc). While it appears that this is the mechanism for the desired biological effect one observes at extremely low dosages, other mechanisms may also contribute to the efficacy of these compounds and the invention is not intended to be bound to any one specific proposed mechanism of action.

In accordance with the invention; oral pharmaceutical compositions are produced by formulating 3-phenoxypyridine or a pharmaceutically acceptable acid-addition salt thereof (as an active ingredient) in dosage unit form with a pharmaceutical carrier. Some examples of dosage unit forms are tablets, capsules, lozenges, and pills; as well as powders and aqueous and non-aqueous solutions and suspensions packaged in containings either one or some larger number of dosage units and capable of being sub-divided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient calculated in the form of its free base, in the foregoing compositions can be varied within wide limits but for practical purposes it is preferably present in a concentration of at least 0.001% in a solid or liquid composition. The most satisfactory compositions are those in which a much higher proportion of the active ingredient is present. The compositions of the invention generally contain from 0.005 mg to 2.1 mg, preferably 0.02 to 1.0 mg of the active ingredient per dosage unit so that the entire amount to be administered during a day can be made up from a reasonable number of dosage units.

Since such extremely low dosages are used, the size by weight or volume of the ultimate dosage form is generally controlled by convenience in preparation and/or use by the subject under treatment. For ease in handling, significant bulking agents would be employed.

Also in accordance with the invention, 3-phenoxypyridine and pharmaceutically-acceptable acid-addition salts thereof are administered for the purpose of treating subjects suffering from a. loss of memory
b. disorientation
c. confusion This invention also teaches the use of 3-phenoxypyridine and phrmaceutically-acceptable acid-addition salts thereof in the treatment of hippocampal dysfunction.

The 3-phenoxypyridine and pharmaceutically-acceptable acid-addition salts thereof may be employed in pharmaceutical compositions in conjunction with other medicaments for the treatment of senility. Examples of such components are N-[2-(diisopropylamino) ethyl]-2-oxo-1-pyrrolidinylacetamide, mixtures of dihydroergo-cornine, dihydroergo-cristine, and dihydroergo-cryptine, 2-oxo-1-pyrrolidinylacetamide, dihydro-1H-pyrrolizine-3,5 (2H,6H) dione, etc. The dosage regimens of these compounds are known and only minor adjustments might be desired when preparing formulations.

The effectiveness of the aforementioned compounds and compositions is determined by the following tests.

A. Reversal of Learning Deficits Produced by Hippocampal Stimulation

The hippocampus is intimately involved with orientation in space and conversion of immediate memory into more permanent memory. Recently, Poschel and Ninteman found that brief bilateral electrical stimulation of the hippocampus of rats produced a transient disruption of learning and memory retrieval in a spatial discrimination task. Further background and rationale for the hippocampal stimulation test is generally described in "Laboratory Animal Science" 27, 738-747 (1977) and "Psychological Reports" 43, 767-770 (1978). The Hippocampal Stimulation test is designed to measure the protective (ameliorative) effects of an organic compound against cognitive deficits (disruption) produced by bilateral electrical stimulation of the hippocampi.

The test subjects are male Long Evans rats. Intracranial electrodes are implanted bilaterally in the hippocampi of male Long Evans rats. The rats are then trained to run back and forth to obtain food pellets at either end of a 152 cm long runway. At the midpoint of the runway are two adjacent doorways. Passing through the correct doorway sets up a food pellet delivery at the end of the runway. Passing through the incorrect doorway merely registers as an error. Test sessions last 25 minutes, with accumulated correct and incorrect runs recorded every five minutes. The doorway designated as correct is changed each day throughout the training and testing periods. On those days when hippocampal stimulation is employed, continuous electrical stimulation is delivered to both electrodes throughout the 25 minute test session.

The subjects are tested once a week, with either an oral dose of a drug or with the drug carrier (water control) one hour prior to testing. On the day before testing, the rats are run without stimulation in a practice session. The rats are their own controls and control tests are run in the sessions just prior to drug testing and again immediately following drug testing. When calculating drug effects the average of both controls is used for each rat. This adjusts for any change in baseline from week to week.

Under the control situation without hippocampal stimulation the normal rat makes about ten percent errors in the test session. The same rat under the influence of hippocampal stimulation makes about 45 percent errors in the test session (50 percent error equates with chance performance). The results obtained by the administration of a 0.010 milligram/kilogram dose of 3-phenoxypyridine monosulfate by the oral (PO) and by the intramuscular route (IM) are recorded in Table 1.

TABLE 1

| Dose mg/kg | n improved N | % Improvement for N | One-tailed t test for paired observations |
|---|---|---|---|
| 0.010 (PO) | 8/8 | +35.0% | t = 4.586, df = 7, p < .005 |
| 0.010 (IM) | 7/8 | +38.9% | t = 3.538, df = 7, p < .01 |

As can be seen, these doses produced a highly significant improvement over the controls.

Surprisingly, when higher doses of CI-844 (in the 5-10 mg/kg range) are employed in the hippocampal stimulation test, the activity disappears as shown in Table 2.

TABLE 2

| Dose mg/kg | n improved N | % Improvement for N | One-tailed t test for paired observations |
|---|---|---|---|
| 5.0 (PO) | 3/6 | -15.0% | Not Significant |
| 10.0 (PO) | 3/6 | +11.0% | Not Significant |

Thus, the above activity is clearly restricted to very low doses of CI-844; higher doses of the drug appear to close the pharmacologic window on this action.

B. Effect on Aged Rat EEG Recorded From Dorsal Hippocampus and Frontal Cortex Since the discovery of quantitative EEG analysis, very subtle changes in the EEG activity of the brain can be measured. In recent years these methods have been applied in man to the study of all major classes of psychopharmacologic drugs, including the so-called nootropic or encephalotropic agents. This recent work as described in "Meth. and Find. Exptl. Clin. Pharmacol.," 2, 269 (1980), "Arzneim-Forsch, 28, 1529 (1978), and Saletu, et al, (1980) has shown that one of the principle central actions of nootropic drugs in man is to promote cerebral vigilance. We recently discovered using power spectra analysis that the EEG profile of the aged Fisher-344 rat recorded from the cortex and hippocampus (See FIGS. 1B and 2B) is consistently different from that of the young rat (Long Evans). (See FIGS. 1A and 2A). The aged rat EEG had dominant high voltage slow wave components in the delta and theta band regions (delta is 2 Hz or less, theta is 4 to 8 Hz). These waves are present in both the cortex and hippocampus. Absent or greatly attenuated in the hippocampus of the aged rat was the dominant theta activity, which was always present in the hippocampus of the young awake rat. The effects of 3-phenoxypyridine monosulfate in this animal model is demonstrated in the following manner.

Aged rats, male Fisher-344 supplied by Harlan Laboratory, are employed. They are intially 20 to 25 months old, weighing approximately 300 to 400 g. The rats are chronically implanted with electrodes: bilaterally in the medial-dorsal hippocampus and epidurally in the frontal cerebral cortices. The hippocampal electrodes are made from 30-gauge platinum wire with 0.5 mm of insulation scraped off at the tip. The frontal cortical electrodes consist of a stainless steel screw, 1.0 mm in diameter, screwed into the skull and brought into contact with the surface of the dura mater. The animal is grounded through a similar stainless steel screw secured to the occipital bone of the skull. All leads are brought to a miniature plug anchored to the rat's skull.

At the time of recording, a commutator device enables the rat to move freely about the floor area of the test chamber 28.5 cm long, 21.5 cm wide, and 45 cm high. Any movement artifacts are eliminated by passing the leads through a tygon tube filled with a saturated NaCl solution (electrically grounded).

The recording system is a 12-channel, model 78D Grass polygraph, with outputs connected to a 12-channel, FM magnetic tape recorder. The analog signals are first electronically summed and then led through a digital FFT computing spectrum analyzer and averager (Nicolet model 446) and finally displayed by the digital plotter with quantitative options. In the EEG spectra, isolated sections (by electronically placed windows) are set as follows—hippocampus: theta bandwidth (4 to 8 Hz); cortex: delta, plus alpha bandwidths (1 to 13 Hz). The unit is read in millivolts root-mean-square (mVrms). Each rat serves as its own control and the results can be expressed in percent change from the predrug control level.

The test session is generally about 180 minutes in length, with EEG samples taken every 30 minutes. These samples consist of 32 successive 8 second epochs analyzed with 400 line resolution. Each of the individual EEG spectral wave analyses therefore represents 4.25 minutes of recording.

The general procedure, then, for testing 3-phenoxypyridine monosulfate is as follows. The rat is connected to the recording leads, placed into the test chamber, and allowed to acclimate to the situation for 1.0 hour. Then a predrug control EEG sample is recorded. (This sample represents the baseline against which all drug effects are evaluated). Immediately thereafter the animal is dosed (generally by oral intubation) and 30 minutes later the first posttreatment EEG sample is recorded. Similar EEG samples are repeated every 30 minutes.

Figure 1A:
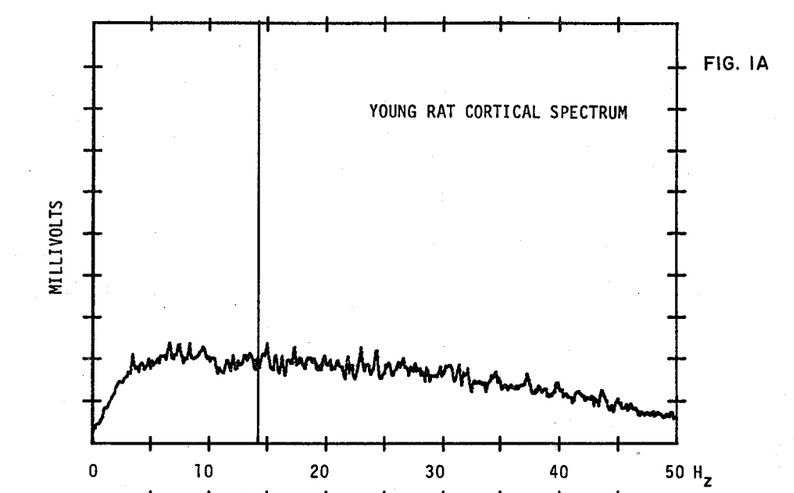
Figure 1B:
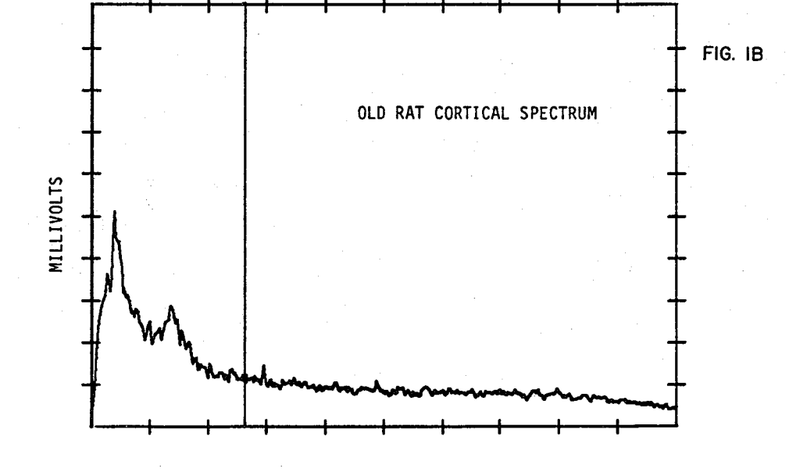
Figure 2A:
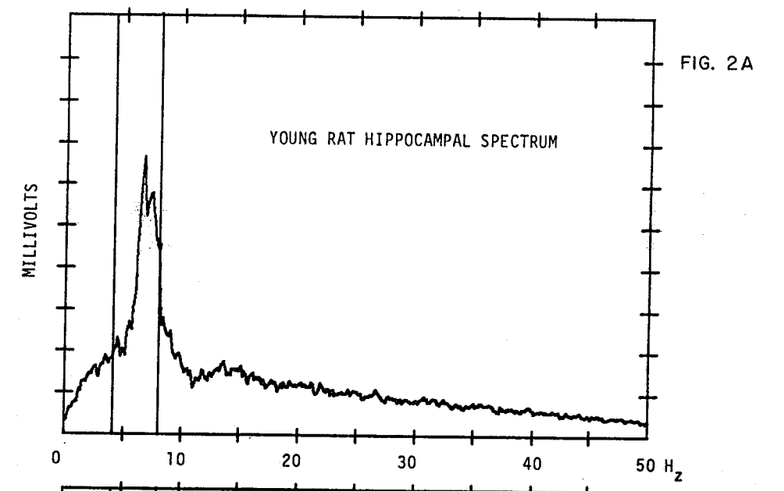
Figure 2B:
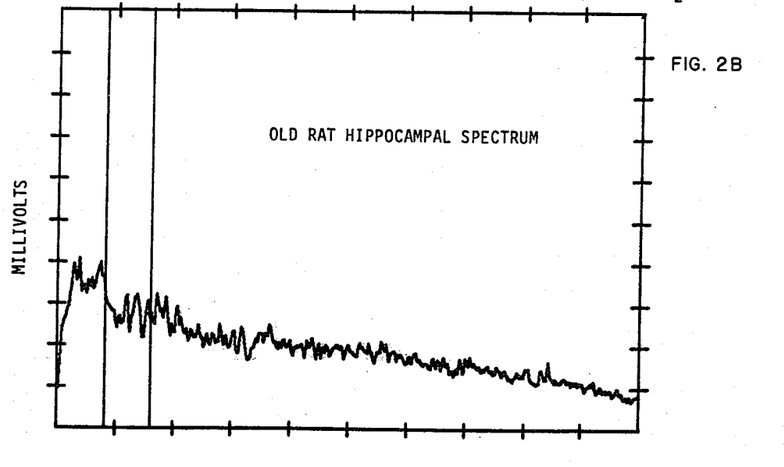

The striking difference in EEG spectral profiles (cortical and hippocampal) between old and young rats can be seen in FIGS. 1 and 2. As can be seen from FIG. 1B, the cortical EEG of the aged rat is dominated by very slow wave (<4 Hz), high voltage activity. The young rat's cortical EEG samples do not show this kind of slow wave activity (FIG. 1A). Equally well, the aged rat's hippocampal EEG activity differs from that of the young rat's. That is, the theta rhythm which is so dominant in the young rat's hippocampus (FIG. 2A) is largely absent in recordings taken from the old rat's hippocampus (FIG. 2B). Moreover, the spectrum analysis in FIG. 2B shows clearly that very slow wave activity (<4 Hz) is very predominant also in th hippocampus (besides in the cortex) of the aged rat.

The above differences in EEG activity between young and old rats are truly representative, having been seen repeatedly in tests of many aged and young rats. These findings indicate that the aged rat brain suffers from a deficit in vigilance similar to that reported in man (studies in humans are restricted to cortical EEGs because of the ethics against implantation of hippocampal recording electrodes).

Figure 3A:
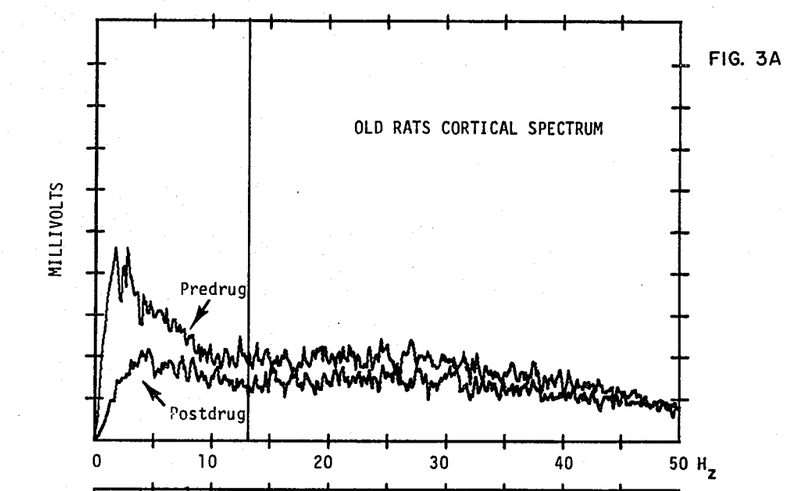
Figure 3B:
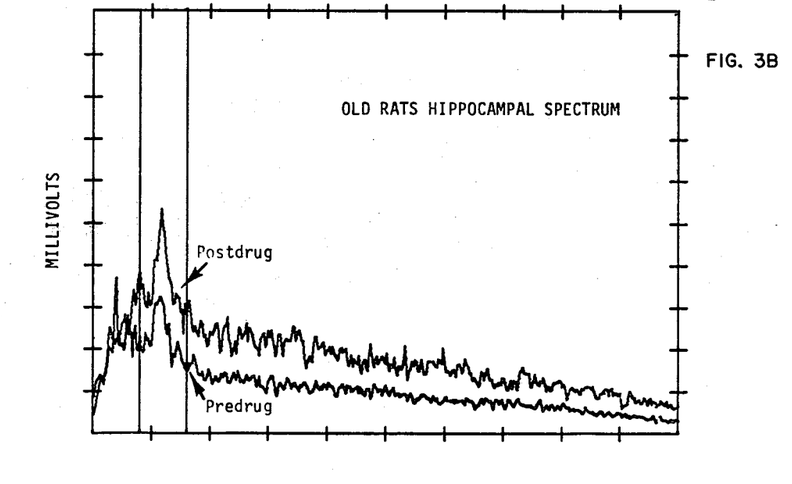
Figure 4A:
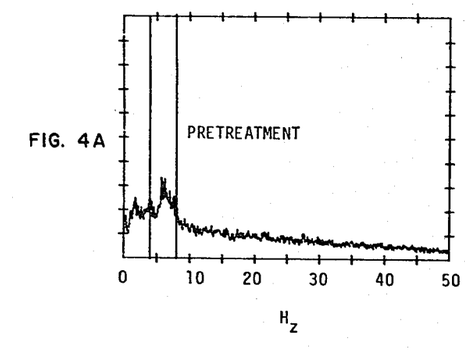
Figure 4B:
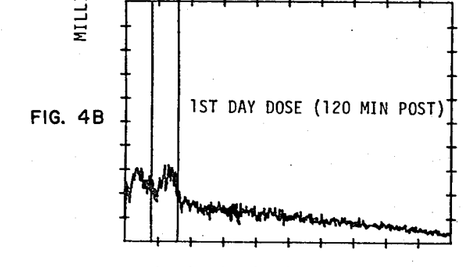
Figure 4C:
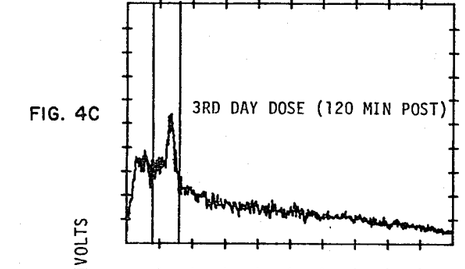
Figure 4D:
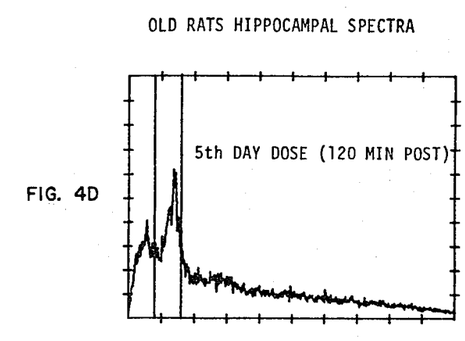
Figure 4W:
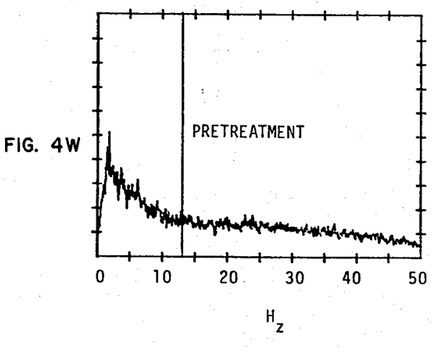
Figure 4X:
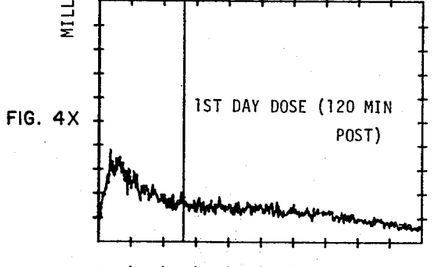
Figure 4Y:
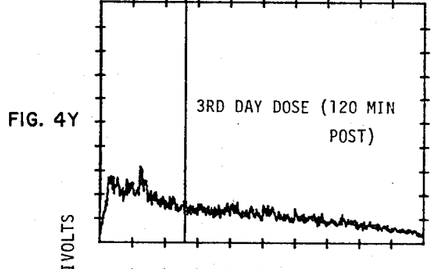
Figure 4Z:
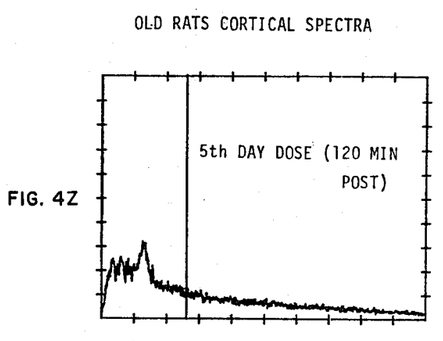

Oran administration of either low dosages or moderate dosages of 3-phenoxypyridine monosulfate to these aged rats caused a startling convergence (see FIG. 3) resulting from administration of 10 mg/kg of 3-phenoxypyridine monosulfate and compare with FIGS. 1 and 2 of the EEG power spectrum towards that of the young rat. FIG. 3 also includes the predrug control spectrum analysis of the same aged rat. The effect of chronic oral dosages of 0.010 mg/kg 3-phenoxypyridine monosulfate, FIG. 4, shows the same results as seen in FIG. 3.

Thus 3-phenoxypyridine and its pharmaceutically acceptable salts are able to cause this starting convergence of the abnormal EEG power spectra of aged rats at surprisingly low dosages.

FIGURE LEGENDS

FIG. 1.
A. Spectrum wave analysis of EEG from cerebral cortex of representative young rat.
B. Identical analysis from represenatative old rat.
FIG. 2.
A. Spectrum wave analysis of EEG from hippocampus of representative young rat.
B. Identical analysis from representative old rat.
FIG. 3.
A. Average (mean) spectrum wave analysis of EEG from cerebral cortex of four old rats before drug treatment and 3.5 hours after oral administration of 10 mg/kg CI-844.
B. Identical analysis from hippocampus.
FIG. 4.
A-D. Average (mean) spectrum wave analysis of EEG from hippocampus of four old rats showing change in hippocampal EEG produced by five consecutive daily oral doses of 0.01 mg/kg CI-844.
W-Z. Identical Analysis from cerebral cortex.

C. THE AMNESIA REVERSAL TEST

The test is designed to show a compound's ability to reverse amnesia produced by electroconvulsive shock. The test is fully described in U.S. Pat. No. 4,145,347, issued Mar. 20, 1979, and is herein incorporated by reference, the only differences being that the test compounds in the present instance are administered orally and the length of electroconvulsive shock is 1.0 seconds.

3-phenoxypyridine monosulfate gives the results reported in Table 3.

TABLE 3

| Dose | % Amnesia Reversal | Rating |
|---|---|---|
| .32000 mg/kg | 83 | A |
| .10000 mg/kg | 58 | A |
| .03200 mg/kg | 0* | N* |
| .01000 mg/kg | 83 | A |
| .00320 mg/kg | 58 | A |
| .00100 mg/kg | 58 | A |
| .00032 mg/kg | 40 | A |
| .00010 mg/kg | 22 | N |
| .00003 mg/kg | 13 | N |

*This result is presumed to be from biological "noise" in the behavioral test method.

The invention is illustrated by the following examples.

EXAMPLE 1

| Ingredient | Quantity |
|---|---|
| 3-Phenoxypyridine Monosulfate | 18.84 g |
| Lactose | 1255.16 g |
| Corn Starch | 39.00 g |
| Hydroxypropyl cellulose | 30.00 g |
| Magnesium stearate | 7.00 g |
| Ethanol-water 50:50 | q.s. |

The 3-phenoxypyridine monosulfate, lactose and hydroxypropyl cellulose are blended and granulated with 50:50 ethanol-water. The wet granulation is screened, dried, and rescreened. The resulting dried granulation is blended with the magnesium stearate and the corn starch, and the mixture is compressed into 225 mg tablets using 11/32 inch standard concave punches. Yield equals approximately 6,000 tablets, each containing 3.14 mg of 3-phenoxypyridine monosulfate equivalent to 2.1 mg of 3-phenoxypyridine base.

By substituting an equivalent amount of another pharmaceutically acceptable 3-phenoxypyridine salt for the 3-phenoxypyridine monosulfate and adjusting the amount of lactose to give the same total weight in the above formula, there are again obtained 225 mg tablets each containing the equivalent of 2.1 mg of 3-phenoxypyridine base.

EXAMPLE 2

| Ingredient | Quantity |
|---|---|
| 3-Phenoxypyridine Monosulfate | .943 g |
| Lactose | 2118.057 g |
| Corn Starch | 60.00 g |
| Hydroxypropyl cellulose | 60.00 g |
| Magnesium stearate | 11.00 g |
| Ethanol-water 50:50 | q.s |

The 3-phenoxypyridine monosulfate, lactose and hydroxypropyl cellulose are blended and granulated with 50:50 ethanol-water. The wet granulation is screened, dried and rescreened. The resulting dried granulation is blended with the magnesium stearate and the corn starch, and the mixture is compressed into 375 mg tablets using 13/32 inch standard concave punches. Yield equals approximately 6,000 tablets, each containing 0.1572 mg of 3-phenoxypyridine base.

By substituting an equivalent amount of another pharmaceutically acceptable 3-phenoxypyridine salt for the 3-phenoxypyridine monosulfate and adjusting the amount of lactose to give the same total weight in the above formula, there are again obtained 375 mg tablets, each containing the equivalent of 0.1 mg of 3-phenoxypyridine base.

EXAMPLE 3

| Ingredient | Quantity |
|---|---|
| 3-Phenoxypyridine Monosulfate | 0.2358 g |
| Lactose | 2801.7642 g |
| Corn Starch | 90 g |
| Hydroxypropyl cellulose | 90 g |
| Magnesium stearate | 18 g |
| Ethanol-water 50:50 | q.s. |

The 3-phenoxypyridine monosulfate, lactose and hydroxypropyl cellulose are blended and granulated with 50:50 ethanol-water. The wet granulation is screened, dried and rescreened. The resulting dried granulation is blended with the magnesium stearate and the corn starch, and the mixture is compressed into 500 mg tablets using ½ inch standard concave punches. Yield equals approximately 6,000 tablets, each containing 393 mg of 3-phenoxypyridine monosulfate equivalent to 250 mg of 3-phenoxypyridine base.

By substituting an equivalent amount of another pharmaceutically acceptable salt of 3-phenoxypyridine for the 3-phenoxypyridine monosulfate and adjusting the above formula, there are again obtained 500 mg tablets, each containing the equivalent of 0.025 mg of 3-phenoxypyridine base.

EXAMPLE 4

| Ingredient | Quantity |
|---|---|
| 3-Phenoxypyridine Monosulfate | 0.393 g |
| Lactose | 1972.607 g |
| Magnesium stearate | 27.000 g |

The mixture is blended and filled into Number Four hard gelatin capsules, filling each capsule with 200 mg of the powder mixture. Yield equals approximately 10,000 capsules, each containing 0.0393 mg of 3-phenoxypyridine monosulfate equivalent to 0.025 mg of 3-phenoxypyridine base.

By substituting an equivalent amount of another pharmaceutically acceptable salt of 3-phenoxypyridine for the 3-phenoxypyridine monosulfate and adjusting the amount of lactose to give the same total weight in the above formula, there are again obtained 200 mg capsules, each containing the equivalent of 0.025 mg of 3-phenoxypyridine base.

EXAMPLE 5

| Ingredient | Quantity |
|---|---|
| 3-Phenoxypyridine Monosulfate | 15.72 g |
| Lactose | 3097.72 g |
| Magnesium stearate | 88.00 g |

The mixture is blended and filled into Number Two hard gelatin capsules filling each capsule with 320 mg of the powder mixture. Yield equals approximately 10,00 capsules, each containing 1.572 mg of 3-phenoxypyridine monosulfate equivalent to 1.0 mg og 3-phenoxypoyridine base.

By substituting an equivalent amount of another pharmaceutically acceptable sale of 3-phenoxypyridine for the 3-phenoxypridine monosulfate and adjusting the amount of lactose to give the same total weight in the above formula, there are again obtained 320 mg capsules, each containing the equivalent of 1.0 mg of 3-phenoxypridine base.

EXAMPLE 6

| Ingredient | Quantity |
|---|---|
| 3-Phenoxypyridine Monosulfate | 7.86 g |
| Lactose | 5622.14 g |
| Magnesium stearate | 170.00 g |

The mixture is blended and filled into Number Zero hard gelatin capsules, filling each capsule with 580 mg of the powder mixture. Yield equal approximately 10,000 capsules, each containing 0.0786 mg of 3-phenoxypridine monosulfate equivalent to 0.050 mg of 3-phenoxypridine base.

By substituting an equivalent amount of another pharmaceutically acceptable 3-phenoxypridine salt for the 3-phenoxypridine monosulfate and adjusting the amount of lactose to give the same total weight in the above formula, there are against obtained 580 mg capsules, each containing the equivalent of 0.050 mg of 3-phenoxypridine base.

EXAMPLE 7

| Ingredient | Quantity |
|---|---|
| 3-Phenoxypyridine | 0.50 g |
| Polyethylene glycol 400 | 1495.50 g |

The above ingredients are blended and filled into soft gelatin capsules, filling each capsule with 300 mg of the mixture. Yield equals approximately 5,000 capsules, each containing 0.1 mg of 3-phenoxypyridine.

We claim:

1. A method for treating memory loss in mammals suffering therefrom which comprises orally administering to said mammals 0.0002 mg to 0.03 mg/kg mammalian body weight of 3-phenoxypyridine or a pharmaceutically acceptable acid addition salt thereof.

2. A method for treating disorientation in mammals suffering therefrom which comprises orally administering to said mammals 0.0002 mg to 0.03 mg/kg mammalian body weight of 3-phenoxypyridine or a pharmaceutically acceptable acid addition salt thereof.

3. A method for treating confusion in mammals suffering therefrom which comprises orally administering to said mammals 0.0002 mg to 0.03 mg/kg mammalian body weight of 3-phenoxypyridine or a pharmaceutically acceptable acid addition salt thereof.

4. A method for treating hippocampal dysfunction in mammals suffering therefrom which comprises orally administering to said mammals 0.0002 mg to 0.03 mg/kg mammalian body weight of 3-phenoxypyridine or a pharmaceutically acceptable acid addition salt thereof.

5. A method of claims 1, 2, 3, or 4 which comprises administering 0.0005 mg to 0.01 mg/kg mammalian body weight of 3-phenoxypyridine or a pharmaceutically-acceptable acid-addition salt thereof.

* * * * *